United States Patent
Sheard et al.

(10) Patent No.: US 8,263,692 B2
(45) Date of Patent: *Sep. 11, 2012

(54) PROPYLENE-BASED POLYMER, ARTICLES, AND PROCESS FOR PRODUCING SAME

(75) Inventors: William G. Sheard, Missouri City, TX (US); Linfeng Chen, Sugar Land, TX (US)

(73) Assignee: Dow Global Technologies LLC, Midland, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 12/650,617

(22) Filed: Dec. 31, 2009

(65) Prior Publication Data

US 2010/0168353 A1    Jul. 1, 2010

Related U.S. Application Data

(60) Provisional application No. 61/141,902, filed on Dec. 31, 2008, provisional application No. 61/141,959, filed on Dec. 31, 2008.

(51) Int. Cl.
*C08F 4/02* (2006.01)
*C08F 110/06* (2006.01)
*C08F 2/00* (2006.01)
*B60C 1/00* (2006.01)

(52) U.S. Cl. ......... 524/287; 526/213; 526/351; 502/127
(58) Field of Classification Search ............... 526/351, 526/213; 502/127; 524/287
See application file for complete search history.

(56) References Cited

U.S. PATENT DOCUMENTS

| 5,674,630 | A | * | 10/1997 | Chatterjee | .................... 428/500 |
| 6,747,103 | B1 | | 6/2004 | Vestberg et al. | |
| 6,825,146 | B2 | | 11/2004 | Kilty et al. | |
| 7,465,776 | B2 | | 12/2008 | Meverden et al. | |
| 2005/0239636 | A1 | * | 10/2005 | Gao et al. | .................... 502/103 |

FOREIGN PATENT DOCUMENTS

WO    03/068828 A1    8/2003

OTHER PUBLICATIONS

Otocka, E.P., et al., Macromolecules, 4, 507-514 (1971).
Scholte, Th. G., et al., J. Appl. Polym. Sci., 29, 3763-3782 (1982).

* cited by examiner

*Primary Examiner* — David W Wu
*Assistant Examiner* — Elizabeth Eng
(74) *Attorney, Agent, or Firm* — Whyte Hirschboeck Dudek SC

(57) ABSTRACT

Disclosed are propylene-based polymer compositions and processes for producing same. Polymerization with an improved catalyst composition provides a propylene-based polymer with improved stiffness.

14 Claims, No Drawings

US 8,263,692 B2

PROPYLENE-BASED POLYMER, ARTICLES, AND PROCESS FOR PRODUCING SAME

PRIORITY CLAIM

This application claims priority to U.S. provisional patent application Ser. No. 61/141,902 filed on Dec. 31, 2008, and U.S. provisional patent application Ser. No. 61/141,959 filed on Dec. 31, 2008, the entire content of each application incorporated by reference herein.

BACKGROUND

The present disclosure relates to compositions and articles containing a propylene-based polymer and processes for producing the same.

Worldwide demand for propylene-based polymers continues to grow as applications for these polymers become more diverse and more sophisticated. Known are Ziegler-Natta catalyst compositions for the production of olefin-based polymers. Ziegler-Natta catalyst compositions typically include a procatalyst containing a transition metal halide (i.e., titanium, chromium, vanadium), a cocatalyst such as an organoaluminum compound, and optionally an external electron donor. Ziegler-Natta catalyzed propylene-based polymers often lack the desired stiffness. Given the perennial emergence of new applications for propylene-based polymers, the art recognizes the need for polymerization processes that produce propylene-based polymers with improved and varied properties. Desirable would be polymerization processes for the production of propylene-based polymers that exhibit high stiffness.

SUMMARY

The present disclosure is directed to propylene-based compositions, articles and processes for producing the same. The propylene-based compositions are produced with a catalyst composition that contains a substituted phenylene aromatic diester, which increases the stiffness of the formant propylene-based polymer.

In an embodiment, the present disclosure is directed to a polymerization process comprising contacting, under polymerization conditions, propylene, and optionally at least one other olefin with a catalyst composition comprising a substituted phenylene aromatic diester; and forming a propylene-based polymer. In an embodiment, the propylene-based polymer has a flexural modulus of greater than 260 kpsi as determined by ASTM D 790. The presence of the substituted phenylene aromatic diester in the catalyst composition yields propylene-based polymer with high stiffness. In an embodiment, the propylene-based polymer is a propylene homopolymer.

The present disclosure provides a composition. In an embodiment, a composition is provided and includes a propylene homopolymer and a substituted phenylene aromatic diester.

The present disclosure provides another composition. In an embodiment, a composition is provided and includes a nonnucleated propylene homopolymer having a polydispersity index less than 6.0, a flexural modulus greater than 283 kpsi and a melt flow rate greater than or equal to 50 g/10 min as measured in accordance with ASTM D 1238 (230° C., 2.16 kg). The propylene homopolymer also includes an oligomer content of less than 1800 ppmw.

The present disclosure provides a propylene impact copolymer. The propylene impact copolymer includes a propylene-based polymer and a substituted phenylene aromatic diester, and a propylene/ethylene copolymer dispersed within the propylene-based polymer.

An advantage of the present disclosure is a polymerization process that uses a catalyst composition that contains a substituted phenylene aromatic diester and produces a propylene-based polymer with a flexural modulus of 260 kpsi or greater.

An advantage of the present disclosure is a polymerization process that produces a propylene-based polymer with high stiffness and a polydispersity index of about 4.0 to about 10.0.

An advantage of the present disclosure is the provision of a propylene impact copolymer composition comprising a substituted phenylene aromatic diester.

An advantage of the present disclosure is the provision of a phthalate-free propylene-based polymer.

DETAILED DESCRIPTION

The present disclosure provides a process. In an embodiment, a polymerization process is provided and includes contacting, under polymerization conditions, propylene and optionally at least one other olefin with a catalyst composition comprising a substituted phenylene aromatic diester. The process includes forming a propylene-based polymer.

In an embodiment, the formant propylene-based polymer has a flexural modulus greater than 260 kpsi as determined by ASTM D 790.

As used herein, "a catalyst composition" is a composition that forms an olefin-based polymer when contacted with an olefin under polymerization conditions. The catalyst composition includes a procatalyst composition, a cocatalyst, optionally an external electron donor, and optionally an activity limiting agent. The procatalyst composition includes a combination of a magnesium moiety, a titanium moiety and an internal electron donor. The internal electron donor includes the substituted phenylene aromatic diester.

The procatalyst composition is produced by halogenating/titanating a procatalyst precursor in the presence of the internal electron donor. As used herein, an "internal electron donor" is a compound added or otherwise formed during formation of the procatalyst composition that donates at least one pair of electrons to one or more metals present in the resultant procatalyst composition. The internal electron donor is the substituted phenylene aromatic diester. Not wishing to be bound by any particular theory, it is believed that during halogenation and titanation the internal electron donor (1) regulates the formation of active sites, (2) regulates the position of titanium on the magnesium-based support and thereby enhances catalyst stereoselectivity, (3) facilitates conversion of the magnesium and titanium moieties into respective halides and (4) regulates the crystallite size of the magnesium halide support during conversion. Thus, provision of the internal electron donor yields a procatalyst composition with enhanced stereoselectivity.

The procatalyst precursor may be a magnesium moiety compound (MagMo), a mixed magnesium titanium compound (MagTi), or a benzoate-containing magnesium chloride compound (BenMag). In an embodiment, the procatalyst precursor is a magnesium moiety ("MagMo") precursor. The "MagMo precursor" contains magnesium as the sole metal component. The MagMo precursor includes a magnesium moiety. Nonlimiting examples of suitable magnesium moieties include anhydrous magnesium chloride and/or its alcohol adduct, magnesium alkoxide or aryloxide, mixed magnesium alkoxy halide, and/or carbonated magnesium dialkoxide or aryloxide. In one embodiment, the MagMo precursor is a magnesium di ($C_{1-4}$)alkoxide. In a further embodiment, the MagMo precursor is diethoxymagnesium.

In an embodiment, the procatalyst precursor is a mixed magnesium/titanium compound ("MagTi"). The "MagTi precursor" has the formula $Mg_dTi(OR^e)_fX_g$ wherein $R^e$ is an aliphatic or aromatic hydrocarbon radical having 1 to 14 carbon atoms or COR' wherein R' is an aliphatic or aromatic hydrocarbon radical having 1 to 14 carbon atoms; each $OR^e$ group is the same or different; X is independently chlorine, bromine or iodine, preferably chlorine; d is 0.5 to 56, or 2 to 4; f is 2 to 116 or 5 to 15; and g is 0.5 to 116, or 1 or 3.

In an embodiment, the procatalyst precursor is a benzoate-containing magnesium chloride material. As used herein, a "benzoate-containing magnesium chloride" ("BenMag") is a magnesium chloride procatalyst (i.e., a halogenated procatalyst precursor) containing a benzoate internal electron donor. The BenMag material may also include a titanium moiety, such as a titanium halide. The benzoate internal donor is labile and can be replaced by other electron donors during procatalyst synthesis. Nonlimiting examples of suitable benzoate groups include ethyl benzoate, methyl benzoate, ethyl p-methoxybenzoate, methyl p-ethoxybenzoate, ethyl p-ethoxybenzoate, ethyl p-chlorobenzoate. In one embodiment, the benzoate group is ethyl benzoate. Nonlimiting examples of suitable BenMag procatalyst precursors include catalysts of the trade names SHAC™ 103 and SHAC™ 310 available from The Dow Chemical Company, Midland, Mich.

In an embodiment, the BenMag procatalyst precursor is a product of halogenation of any procatalyst precursor (i.e., a MagMo precursor or a MagTi precursor) in the presence of a benzoate compound with the structure (I)

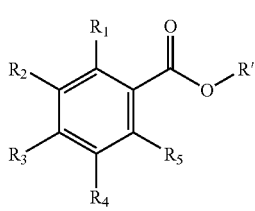

(I)

wherein $R_1$-$R_5$ are H, $C_1$-$C_{20}$ hydrocarbyl which may contain heteroatoms including F, Cl, Br, I, O, S, N, P, and Si, and R' is a $C_1$-$C_{20}$ hydrocarbyl group which may optionally contain heteroatom(s) including F, Cl, Br, I, O, S, N, P, and Si. Preferably, $R_1$-$R_5$ are selected from H and $C_1$-$C_{20}$ alkyl and R' is selected from $C_1$-$C_{20}$ alkyl and alkoxyalkyl.

Halogenation/titanation of the procatalyst precursor in the presence of the internal electron donor produces a procatalyst composition which includes a combination of a magnesium moiety, a titanium moiety, and the internal electron donor (a substituted phenylene aromatic diester). In an embodiment, the magnesium and titanium moieties are respective halides, such as magnesium chloride and titanium chloride. Bounded by no particular theory, it is believed that the magnesium halide is a support upon which the titanium halide is deposited and into which the internal electron donor is incorporated.

The resulting procatalyst composition has a titanium content of from about 1.0 percent by weight to about 6.0 percent by weight, based on the total solids weight, or from about 1.5 percent by weight to about 5.5 percent by weight, or from about 2.0 percent by weight to about 5.0 percent by weight. The weight ratio of titanium to magnesium in the solid procatalyst composition is suitably between about 1:3 and about 1:160, or between about 1:4 and about 1:50, or between about 1:6 and 1:30. The internal electron donor is present in an amount from about 0.1 wt % to about 20.0 wt %, or from about 1.0 wt % to about 15 wt %. The internal electron donor may be present in the procatalyst composition in a molar ratio of internal electron donor to magnesium of from about 0.005:1 to about 1:1, or from about 0.01:1 to about 0.4:1. Weight percent is based on the total weight of the procatalyst composition.

Ethoxide content in the procatalyst composition indicates the completeness of conversion of precursor metal ethoxide into a metal halide. The halogenated amide ester assists in converting ethoxide into halide during halogenation. In an embodiment, the procatalyst composition includes from about 0.01 wt % to about 1.0 wt %, or from about 0.05 wt % to about 0.5 wt % ethoxide. Weight percent is based on the total weight of the procatalyst composition.

In an embodiment, the internal electron donor is a mixed internal electron donor. As used herein, a "mixed internal electron donor" is (i) a substituted phenylene aromatic diester, (ii) an electron donor component that donates a pair of electrons to one or more metals present in the resultant procatalyst composition, and (iii) optionally other components. In an embodiment, the electron donor component is a benzoate, such as ethyl benzoate and/or methoxypropan-2-yl benzoate. The procatalyst composition with the mixed internal electron donor can be produced by way of the procatalyst production procedure as previously disclosed.

The internal electron donor includes the substituted phenylene aromatic diester and optionally an electron donor component (such as a diether and/or a benzoate). The substituted phenylene aromatic diester may be a substituted 1,2-phenylene aromatic diester, a substituted 1,3 phenylene aromatic diester, or a substituted 1,4 phenylene aromatic diester. In an embodiment, a 1,2-phenylene aromatic diester is provided. The substituted 1,2-phenylene aromatic diester has the structure (II) below:

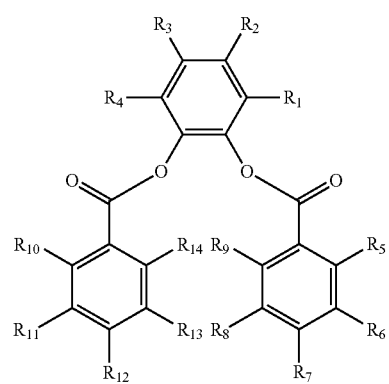

(II)

wherein $R_1$-$R_{14}$ are the same or different. Each of $R_1$-$R_{14}$ is selected from a hydrogen, substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof. At least one of $R_1$-$R_{14}$ is not hydrogen.

As used herein, the term "hydrocarbyl" and "hydrocarbon" refer to substituents containing only hydrogen and carbon atoms, including branched or unbranched, saturated or unsaturated, cyclic, polycyclic, fused, or acyclic species, and combinations thereof. Nonlimiting examples of hydrocarbyl groups include alkyl-, cycloalkyl-, alkenyl-, alkadienyl-, cycloalkenyl-, cycloalkadienyl-, aryl-, aralkyl, alkylaryl, and alkynyl-groups.

As used herein, the terms "substituted hydrocarbyl" and "substituted hydrocarbon" refer to a hydrocarbyl group that is substituted with one or more nonhydrocarbyl substituent groups. A nonlimiting example of a nonhydrocarbyl substituent group is a heteroatom. As used herein, a "heteroatom" refers to an atom other than carbon or hydrogen. The heteroatom can be a non-carbon atom from Groups IV, V, VI, and VII of the Periodic Table. Nonlimiting examples of heteroatoms include: halogens (F Cl, Br, I), N, O, P, B, S, and Si. A substituted hydrocarbyl group also includes a halohydrocarbyl group and a silicon-containing hydrocarbyl group. As used herein, the term "halohydrocarbyl" group refers to a hydrocarbyl group that is substituted with one or more halogen atoms. As used herein, the term "silicon-containing hydrocarbyl group" is a hydrocarbyl group that is substituted with one or more silicon atoms. The silicon atom(s) may or may not be in the carbon chain.

In an embodiment, at least one (or two, or three, or four) R group(s) of $R_1$-$R_4$ is selected from a substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof.

In an embodiment, at least one (or some, or all) R group(s) of $R_5$-$R_{14}$ is selected from a substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof. In another embodiment, at least one of $R_5$-$R_9$ and at least one of $R_{10}$-$R_{14}$ is selected from a substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof.

In an embodiment, at least one of $R_1$-$R_4$ and at least one of $R_5$-$R_{14}$ is selected from a substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof. In another embodiment, at least one of $R_1$-$R_4$ at least one $R_5$-$R_9$ of and at least one of $R_{10}$-$R_{14}$ is selected from a substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof.

In an embodiment, any consecutive R groups in $R_1$-$R_4$, and/or any consecutive R groups in $R_5$-$R_9$, and/or any consecutive R groups in $R_{10}$-$R_{14}$ may be linked to form an inter-cyclic or an intra-cyclic structure. The inter-/intra-cyclic structure may or may not be aromatic. In an embodiment, the inter-/intra-cyclic structure is a $C_5$ or a $C_6$ membered ring.

In an embodiment, at least one of $R_1$-$R_4$ is selected from a substituted hydrocarbyl group having 1 to 20 carbon atoms, an unsubstituted hydrocarbyl group having 1 to 20 carbon atoms, and combinations thereof. Optionally, at least one of $R_5$-$R_{14}$ may be a halogen atom or an alkoxy group having 1 to 20 carbon atoms. Optionally, $R_1$-$R_4$, and/or $R_5$-$R_9$, and/or $R_{10}$-$R_{14}$ may be linked to form an inter-cyclic structure or an intra-cyclic structure. The inter-cyclic structure and/or the intra-cyclic structure may or may not be aromatic.

In an embodiment, any consecutive R groups in $R_1$-$R_4$, and/or in $R_5$-$R_9$, and/or in $R_{10}$-$R_{14}$, may be members of a $C_5$-$C_6$-membered ring.

In an embodiment, structure (II) includes $R_1$, $R_3$ and $R_4$ as hydrogen. $R_2$ is selected from a substituted hydrocarbyl group having 1 to 20 carbon atoms, an unsubstituted hydrocarbyl group having 1 to 20 carbon atoms, and combinations thereof. $R_5$-$R_{14}$ are the same or different and each of $R_5$-$R_{14}$ is selected from hydrogen, a substituted hydrocarbyl group having 1 to 20 carbon atoms, an unsubstituted hydrocarbyl group having 1 to 20 carbon atoms, an alkoxy group having 1 to 20 carbon atoms, a halogen, and combinations thereof.

In an embodiment, structure (II) includes $R_2$ that is methyl, and each of $R_5$-$R_{14}$ is hydrogen.

In an embodiment, structure (II) includes $R_2$ that is ethyl, and each of $R_5$-$R_{14}$ is hydrogen.

In an embodiment, structure (II) includes $R_2$ that is t-butyl, and each of $R_5$-$R_{14}$ is hydrogen.

In an embodiment, structure (II) includes $R_2$ that is ethoxycarbonyl, and each of $R_5$-$R_{14}$ is hydrogen.

In an embodiment, structure (II) includes $R_2$, $R_3$ and $R_4$ each as hydrogen and $R_1$ is selected from a substituted hydrocarbyl group having 1 to 20 carbon atoms, an unsubstituted hydrocarbyl group having 1 to 20 carbon atoms, and combinations thereof. $R_5$-$R_{14}$ are the same or different and each is selected from hydrogen, a substituted hydrocarbyl group having 1 to 20 carbon atoms, an unsubstituted hydrocarbyl group having 1 to 20 carbon atoms, an alkoxy group having 1 to 20 carbon atoms, a halogen, and combinations thereof.

In an embodiment, structure (II) includes $R_1$ that is methyl, and each of $R_5$-$R_{14}$ is hydrogen.

In an embodiment, structure (II) includes $R_2$ and $R_4$ that are hydrogen and $R_1$ and $R_3$ are the same or different. Each of $R_1$ and $R_3$ is selected from a substituted hydrocarbyl group having 1 to 20 carbon atoms, an unsubstituted hydrocarbyl group having 1 to 20 carbon atoms, and combinations thereof. $R_5$-$R_{14}$ are the same or different and each of $R_5$-$R_{14}$ is selected from a substituted hydrocarbyl group having 1 to 20 carbon atoms, an unsubstituted hydrocarbyl group having 1 to 20 carbon atoms, an alkoxy group having 1 to 20 carbon atoms, a halogen, and combinations thereof.

In an embodiment, structure (II) includes $R_1$ and $R_3$ that are the same or different. Each of $R_1$ and $R_3$ is selected from a $C_1$-$C_8$ alkyl group, a $C_3$-$C_6$ cycloalkyl group, or a substituted $C_3$-$C_6$ cycloalkyl group. $R_5$-$R_{14}$ are the same or different and each of $R_5$-$R_{14}$ is selected from hydrogen, a $C_1$-$C_8$ alkyl group, and a halogen. Nonlimiting examples of suitable $C_1$-$C_8$ alkyl groups include methyl, ethyl, n-propyl, isopropyl, n-butyl, i-butyl, t-butyl, n-pentyl, i-pentyl, neopentyl, t-pentyl, n-hexyl, and 2,4,4-trimethylpentan-2-yl group. Nonlimiting examples of suitable $C_3$-$C_6$ cycloalkyl groups include cyclopentyl and cyclohexyl groups. In a further embodiment, at least one of $R_5$-$R_{14}$ is a $C_1$-$C_6$ alkyl group or a halogen.

In an embodiment, structure (II) includes $R_1$ that is a methyl group and $R_3$ that is a t-butyl group. Each of $R_2$, $R_4$ and $R_5$-$R_{14}$ is hydrogen.

In an embodiment, structure (II) includes $R_1$ and $R_3$ that is an isopropyl group. Each of $R_2$, $R_4$ and $R_5$-$R_{14}$ is hydrogen.

In an embodiment, structure (II) includes each of $R_1$, $R_5$, and $R_{10}$ as a methyl group and $R_3$ is a t-butyl group. Each of $R_2$, $R_4$, $R_6$-$R_9$ and $R_{11}$-$R_{14}$ is hydrogen.

In an embodiment, structure (II) includes each of $R_1$, $R_7$, and $R_{12}$ as a methyl group and $R_3$ is a t-butyl group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ as a methyl group and $R_3$ is a t-butyl group. Each of $R_7$ and $R_{12}$ is an ethyl group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes each of $R_1$, $R_5$, $R_7$, $R_9$, $R_{10}$, $R_{12}$, and $R_{14}$ as a methyl group and $R_3$ is a t-butyl group. Each of $R_2$, $R_4$, $R_6$, $R_8$, $R_{11}$, and $R_{13}$ is hydrogen.

In an embodiment, structure (II) includes $R_1$ as a methyl group and $R_3$ is a t-butyl group. Each of $R_5$, $R_7$, $R_9$, $R_{10}$, $R_{12}$, and $R_{14}$ is an i-propyl group. Each of $R_2$, $R_4$, $R_6$, $R_8$, $R_{11}$, and $R_{13}$ is hydrogen.

In an embodiment, the substituted phenylene aromatic diester has a structure (III) which includes $R_1$ that is a methyl group and $R_3$ is a t-butyl group. Each of $R_2$ and $R_4$ is hydrogen. $R_8$ and $R_9$ are members of a $C_6$ membered ring to form a 1-naphthoyl moiety. $R_{13}$ and $R_{14}$ are members of a $C_6$ membered ring to form another 1-naphthoyl moiety. Structure (III) is provided below.

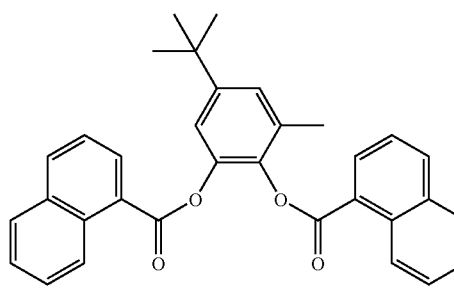

(III)

In an embodiment, the substituted phenylene aromatic diester has a structure (IV) which includes $R_1$ that is a methyl group and $R_3$ is a t-butyl group. Each of $R_2$ and $R_4$ is hydrogen. $R_6$ and $R_7$ are members of a $C_6$ membered ring to form a 2-naphthoyl moiety. $R_{12}$ and $R_{13}$ are members of a $C_6$ membered ring to form a 2-naphthoyl moiety. Structure (IV) is provided below.

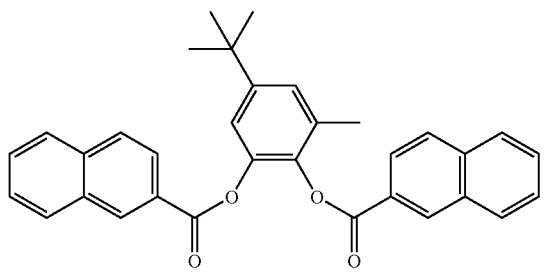

(IV)

In an embodiment, structure (II) includes $R_1$ that is a methyl group and $R_3$ is a t-butyl group. Each of $R_7$ and $R_{12}$ is an ethoxy group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is a fluorine atom. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is a chlorine atom. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is a bromine atom. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is an iodine atom. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_6$, $R_7$, $R_{11}$, and $R_{12}$ is a chlorine atom. Each of $R_2$, $R_4$, $R_5$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_6$, $R_8$, $R_{11}$, and $R_{13}$ is a chlorine atom. Each of $R_2$, $R_4$, $R_5$, $R_7$, $R_9$, $R_{10}$, $R_{12}$, and $R_{14}$ is hydrogen.

In an embodiment, structure (II) includes $R_1$ that is a methyl group and $R_3$ is a t-butyl group. Each of $R_2$, $R_4$ and $R_5$-$R_{14}$ is a fluorine atom.

In an embodiment, structure (II) includes $R_1$ that is a methyl group and $R_3$ is a t-butyl group. Each of $R_7$ and $R_{12}$ is a trifluoromethyl group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is an ethoxycarbonyl group. Each of $R_2$, $R_4$, $R_5$, $R_6$, $R_8$, $R_9$, $R_{10}$, $R_{11}$, $R_{13}$, and $R_{14}$ is hydrogen.

In an embodiment, $R_1$ is methyl group and $R_3$ is a t-butyl group. Each of $R_7$ and $R_{12}$ is an ethoxy group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is a diethylamine group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a 2,4,4-trimethylpentan-2-yl group. Each of $R_2$, $R_4$ and $R_5$-$R_{14}$ is hydrogen.

In an embodiment, structure (II) includes $R_1$ and $R_3$, each of which is a sec-butyl group. Each of $R_2$, $R_4$ and $R_5$-$R_{14}$ is hydrogen.

In an embodiment, the substituted phenylene aromatic diester has a structure (V) whereby $R_1$ and $R_2$ are members of a $C_6$ membered ring to form a 1,2-naphthalene moiety. Each of $R_5$-$R_{14}$ is hydrogen. Structure (V) is provided below.

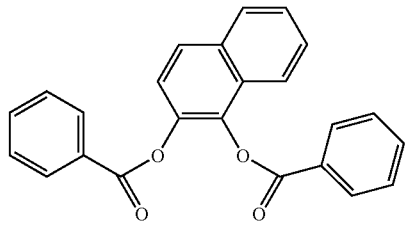

(V)

In an embodiment, the substituted phenylene aromatic diester has a structure (VI) whereby $R_2$ and $R_3$ are members of a $C_6$ membered ring to form a 2,3-naphthalene moiety. Each of $R_5$-$R_{14}$ is hydrogen. Structure (VI) is provided below.

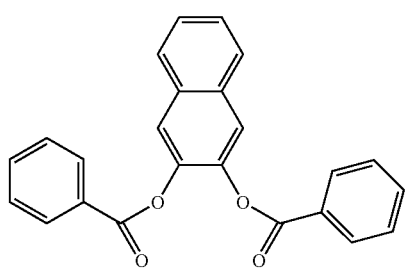

(VI)

In an embodiment, structure (II) includes $R_1$ and $R_4$ that are each a methyl group. Each of $R_2$, $R_3$, $R_5$-$R_9$ and $R_{10}$-$R_{14}$ is hydrogen.

In an embodiment, structure (II) includes $R_1$ that is a methyl group. $R_4$ is an i-propyl group. Each of $R_2$, $R_3$, $R_5$-$R_9$ and $R_{10}$-$R_{14}$ is hydrogen.

In an embodiment, structure (II) includes $R_1$, $R_3$, and $R_4$, each of which is an i-propyl group. Each of $R_2$, $R_5$-$R_9$ and $R_{10}$-$R_{14}$ is hydrogen.

The catalyst composition includes a cocatalyst. As used herein, a "cocatalyst" is a substance capable of converting the procatalyst to an active polymerization catalyst. The cocatalyst may include hydrides, alkyls, or aryls of aluminum, lithium, zinc, tin, cadmium, beryllium, magnesium, and combinations thereof. In an embodiment, the cocatalyst is a hydrocarbyl aluminum compound represented by the formula $R_nAlX_{3-n}$ wherein n=1 2, or 3, R is an alkyl, and X is a halide or alkoxide. Nonlimiting examples of suitable cocatalyst include from trimethylaluminum, triethylaluminum, tri-isobutylaluminum, and tri-n-hexylaluminum.

In an embodiment, the cocatalyst is triethylaluminum. The molar ratio of aluminum to titanium is from about 5:1 to about 500:1, or from about 10:1 to about 200:1, or from about 15:1 to about 150:1, or from about 20:1 to about 100:1, or from about 30:1 to about 60:1. In another embodiment, the molar ratio of aluminum to titanium is about 35:1.

In an embodiment, the present catalyst composition includes an external electron donor. As used herein, an "external electron donor" (or "EED") is a compound added independent of procatalyst formation and includes at least one functional group that is capable of donating a pair of electrons to a metal atom. A "mixed external electron donor" (or "MEED") is a mixture of two or more external electron donors. Bounded by no particular theory, it is believed that provision of one or more external electron donors in the catalyst composition affects the following properties of the formant polymer: level of tacticity (i.e., xylene soluble material), molecular weight (i.e., melt flow), molecular weight distribution (MWD), melting point, and/or oligomer level.

In an embodiment, the external electron donor may be selected from one or more of the following: a silicon compound, a bidentate compound, an amine, an ether, a carboxylate, a ketone, an amide, a carbamate, a phosphine, a phosphate, a phosphite, a sulfonate, a sulfone, a sulfoxide, and any combination of the foregoing.

In an embodiment, the EED is a silicon compound having the general formula (VII):

$$SiR_m(OR')_{4-m} \qquad (VII)$$

wherein R independently each occurrence is hydrogen or a hydrocarbyl or an amino group, optionally substituted with one or more substituents containing one or more Group 14, 15, 16, or 17 heteroatoms. R contains up to 20 atoms not counting hydrogen and halogen. R' is a $C_{1-20}$ alkyl group, and m is 0, 1, or 2. In an embodiment, R is $C_{6-12}$ aryl, alkylaryl or aralkyl, $C_{3-12}$ cycloallyl, $C_{1-20}$ linear alkyl or alkenyl, $C_{3-12}$ branched alkyl, or $C_{3-12}$ cyclic amino group, R' is $C_{1-4}$ alkyl, and m is 1 or 2.

Nonlimiting examples of suitable silicon compounds for the EED include dialkoxysilanes, trialkoxysilanes, and tetraalkoxysilanes such as dicyclopentyldimethoxysilane, diisopropyldimethoxysilane, bis(perhydroisoquinolino)dimethoxysilane, methylcyclohexyldimethoxysilane, tetraethoxysilane, n-propyltrimethoxysilane, n-propyltriethoxysilane, diethylaminotriethoxysilane, bis(trimethylsilylmethyl)dimethoxysilane, and any combination thereof.

In an embodiment, the catalyst composition includes an activity limiting agent (ALA). As used herein, an "activity limiting agent" ("ALA") is a material that reduces catalyst activity at elevated temperature (i.e., temperature greater than about 85° C.). An ALA inhibits or otherwise prevents polymerization reactor upset and ensures continuity of the polymerization process. Typically, the activity of Ziegler-Natta catalysts increases as the reactor temperature rises. Ziegler-Natta catalysts also typically maintain high activity near the softening point temperature of the polymer produced. The heat generated by the exothermic polymerization reaction may cause polymer particles to form agglomerates and may ultimately lead to disruption of continuity for the polymer production process. The ALA reduces catalyst activity at elevated temperature, thereby preventing reactor upset, reducing (or preventing) particle agglomeration, and ensuring continuity of the polymerization process.

The ALA may or may not be a component of the EED and/or the MEED. The activity limiting agent may be a carboxylic acid ester, a diether, a poly(alkene glycol), a succinate, a diol ester, and combinations thereof. The carboxylic acid ester can be an aliphatic or aromatic, mono- or poly-carboxylic acid ester. Nonlimiting examples of suitable carboxylic acid esters include benzoates, $C_{1-40}$ alkyl esters of aliphatic $C_{2-40}$ mono-/di-carboxylic acids, $C_{2-40}$ mono-/polycarboxylate derivatives of $C_{2-100}$ (poly)glycols, $C_{2-100}$ (poly)glycol ethers, and any combination thereof. Further nonlimiting examples of carboxylic acid esters include laurates, myristates, palmitates, stearates, oleates, sebacates, and (poly)(alkylene)glycols, and mixtures thereof. In a further embodiment, the ALA is isopropyl myristate or di-n-butyl sebacate.

The catalyst composition may include any of the foregoing external electron donors in combination with any of the foregoing activity limiting agents. The external electron donor and/or activity limiting agent can be added into the reactor separately. Alternatively, the external electron donor and the activity limiting agent can be mixed together in advance and then added to the catalyst composition and/or into the reactor as a mixture.

The process includes contacting, under polymerization conditions, propylene, and optionally at least one other olefin, with the catalyst composition containing the substituted phenylene aromatic diester. As used herein, "polymerization conditions" are temperature and pressure parameters within a polymerization reactor suitable for promoting polymerization between the catalyst composition and an olefin to form the desired polymer. The polymerization process may be a gas phase, a slurry, or a bulk polymerization process, operating in one, or more than one reactor.

It is understood that provision of hydrogen in the polymerization reactor is a component of the polymerization conditions. During polymerization, hydrogen is a chain transfer agent and affects the molecular weight (and correspondingly the melt flow rate) of the resultant polymer. The polymerization process may include a pre-polymerization step and/or a pre-activation step.

The process includes forming a propylene-based polymer. The propylene based polymer includes a substituted phenylene aromatic diester. In an embodiment, the propylene-based polymer has a flexural modulus of greater than 260 kpsi to 290 kpsi, or 260 kpsi to 280 kpsi, or 260 kpsi to 270 kpsi as determined by ASTM D 790.

Applicants surprisingly discovered that the provision of the substituted phenylene aromatic diester in the catalyst composition unexpectedly forms a propylene-based polymer having high-stiffness and a polydispersity index less than 8.0, or about 5.0. In an embodiment, the substituted phenylene aromatic diester is 3-methyl-5-tert butyl-1,2 phenylene dibenzoate.

In an embodiment, the process includes adding an ALA during the contacting phase of the process. One or more than one ALA may be added. In an embodiment, the ALA is isopropyl myristate.

In an embodiment, the catalyst composition used during the process comprises a substituted phenylene aromatic diester, aluminum and an external electron donor (EED). The EED can be dicyclopentyldimethoxysilane (DCPDMS).

In an embodiment, the EED and aluminum are maintained at a molar ratio of less than 5.0, or less than 4.0, or less than 3.0 during the contacting. Maintaining this molar ratio may be accomplished by (i) pre-mixing the EED with the catalyst and/or cocatalyst prior to introduction into the reactor, (ii) separately adding cocatalyst and/or EED to the polymerization reactor in response to reactor/polymerization conditions.

In an embodiment, the process further comprises nucleating the formed propylene polymer, and producing a nucleated propylene-based polymer with a flexural modulus of 300 kpsi to 380 kpsi, or 300 kpsi to 360 kpsi, or 300 kpsi to 340 kpsi, or 300 kpsi to 332 kpsi, or 300 kpsi to 325 kpsi as determined by ASTM D 790. As used herein, "nucleation" is the process by which compounds and compositions are used to produce faster crystallization and/or higher polymer crystallization temperatures. Nucleation is a post-reactor procedure whereby a nucleating agent is blended (typically melt blended) with the propylene-based polymer. As used herein, "nucleating agents" are compounds utilized to provide nucleation sites for crystal growth during cooling of a polyolefin molten formulation. Nucleating agents increase the rate at which nucleation events occur, often enabling significant crystallization at temperatures higher than possible in the absence of such an agent. Nucleation increases polymer stiffness. A "nucleated propylene-based polymer" is a polymer that has been subjected to nucleation. A "non-nucleated propylene-based polymer" is a polymer that has not been subjected to nucleation.

Nonlimiting examples of suitable nucleating agents include 1,3-O-2,4-bis(3,4-dimethylbenzylidene)sorbitol (hereinafter DMDBS), available from Milliken Chemical under the trade name Millad® 3988, sodium benzoate, sodium 2,2'-methylene-bis-(4,6-di-tert-butylphenyl)phosphate (from Asahi Denka Kogyo K. K., known as NA-11), aluminum bis[2,2'-methylene-bis-(4,6-di-tert-butylphenyl) phosphate] (also from Asahi Denka Kogyo K. K., known as NA-21), talc, and the like.

In an embodiment, the process includes forming a propylene-based polymer having a melt flow rate (MFR) from 0.1 g/10 min to 500 g/10 min, or from 20 g/10 min to 400 g/10 min, or from 40 g/10 min to 300 g/10 min, or from 50 g/10 min to about 100 g/10 min. In a further embodiment, the propylene-based polymer is a propylene homopolymer (i.e., polypropylene or polypropylene homopolymer).

In an embodiment, the process includes forming a propylene-based polymer having a xylene solubles content from 0.5 wt % to 10 wt %, or from 1 wt % to 8 wt %, or from 1 wt % to 5 wt %, or from 1 wt % to 3 wt %, or from 1 wt % to 1.5 wt %. In a further embodiment, the propylene-based polymer is a propylene homopolymer. Weight percent is based on total weight of the propylene-based polymer.

In an embodiment, the process includes forming a propylene-based polymer having a polydispersity index (PDI) from about 4.0 to about 10.0, or from about 4.0 to about 8.0, or from about 4.0 to about 6.0. In a further embodiment, the propylene-based polymer is a propylene homopolymer.

In an embodiment, the process includes forming a propylene-based polymer having an isotactic block length of 350-500, or 350-450, or 350-400. In a further embodiment, the propylene-based polymer is a propylene homopolymer.

In an embodiment, the process includes forming a propylene-based polymer having an oligomer content of less than 1800 parts per million by weight (ppmw), or less than 1600 ppmw, or less than 1400 ppmw, or less than 1200 ppmw, or from 800 ppmw to less than 1800 ppmw as determined at a melt flow rate of 50 g/10 min. In a further embodiment, the propylene-based polymer is a propylene homopolymer.

In an embodiment, the process includes forming a propylene-based polymer having isotactic (mmmm) pentads higher than 93-99%, or 93-97%, or 93-95% as determined by $^{13}C$-NMR analysis.

One or more olefin comonomers can be introduced into a polymerization reactor along with the propylene to react with the catalyst composition and to form a polymer, or a fluidized bed of polymer particles. Nonlimiting examples of suitable olefin monomers include ethylene (for purposes of this disclosure, ethylene is considered an α-olefin), $C_{4-20}$ α-olefins, such as 1-butene, 1-pentene, 1-hexene, 4-methyl-1-pentene, 1-heptene, 1-octene, 1-decene, 1-dodecene and the like. In an embodiment, the olefin comonomer is ethylene.

In an embodiment, a propylene homopolymer is produced in a first reactor. The content of the first reactor is subsequently transferred to a second reactor into which at least one olefin is introduced. This results in production of a propylene impact copolymer in the second reactor.

In an embodiment, a propylene homopolymer is formed via introduction of propylene and any of the present catalyst compositions, cocatalysts, external electron donors, and activity limiting agents in the first reactor. The propylene homopolymer is introduced into the second reactor along with ethylene (alone or with propylene) and optionally an external electron donor and/or an activity limiting agent. The external electron donor and the activity limiting agent may be the same as or different from the respective components used in the first reactor. This produces a propylene-ethylene copolymer in the second reactor. The propylene/ethylene copolymer is dispersed (discontinuous phase) in the propylene-based polymer (continuous phase), active catalyst within the propylene-based polymer drives the polymerization of the propylene/ethylene copolymer. Therefore, the substituted phenylene aromatic diester is present in the propylene-based polymer and the propylene/ethylene copolymer.

The propylene impact copolymer includes a propylene-based polymer and a substituted phenylene aromatic diester; and a propylene/ethylene copolymer dispersed within the propylene-based polymer. A substituted phenylene aromatic diester is present in the propylene homopolymer and/or the propylene/ethylene copolymer. In an embodiment, the substituted phenylene aromatic diester is 3-methyl-5-tert butyl-1,2 phenylene dibenzoate.

In an embodiment, the propylene impact copolymer in the propylene-based polymer of the propylene impact copolymer has a polydispersity index of 8.0 or less. The propylene-based polymer of the propylene impact copolymer has a xylene soluble content less than or equal to 1.5% by weight.

The present process produces a composition. In an embodiment, a composition is provided and includes a propylene-based polymer. The propylene-based polymer includes a substituted phenylene aromatic diester. The propylene-based polymer may be any propylene-based polymer (nucleated/non-nucleated) as previously disclosed herein with one or more of the properties as previously disclosed herein. In an embodiment the composition is a propylene homopolymer.

In an embodiment, the substituted phenylene aromatic diester of the composition is 3-methyl-5-tert butyl-1,2 phenylene dibenzoate.

In an embodiment, the propylene-based polymer of the composition has one or more of the following properties with ranges/subranges as previously disclosed herein: a flexural modulus of greater than 260 kpsi to 290 kpsi, a polydispersity of 8.0 or less, a xylene soluble content from 0.5 wt % to less than or equal to 1.5 wt %, an isotactic (mmmm) pentads higher than 97%, a MFR from 50 g/10 min to 100 g/10 min, and/or an oligomer content less than 1800 ppmw.

The present disclosure provides another composition. The composition may be produced by any of the foregoing processes. In an embodiment, a composition is provided and includes a non-nucleated propylene homopolymer having a polydispersity index of less than 6.0. The propylene homopolymer also has a flexural modulus greater than 283 kpsi and a melt flow rate greater than or equal to 50 g/10 min as measured in accordance with ASTM D 1238 (230° C., 2.16 kg). The propylene homopolymer also has an oligomer content of less than 1800 ppmw, or from about 800 ppmw to less than 1800 ppmw.

In an embodiment, the propylene-based polymer has a xylene soluble content less than or equal to 1.5% by weight.

In an embodiment, the composition includes a substituted phenylene aromatic diester. The substituted phenylene aromatic diester is 3-methyl-5-tert butyl-1,2 phenylene dibenzoate.

In an embodiment, the composition may include one or more of the following additives: stabilizers, lubricants, mold release agents, fillers, nucleating agents, antistatics, plasticizers, dyes, pigments, antifungals, anti-microbial agents, film cavitating agents, flame retardants, and any combination of the foregoing.

In an embodiment, the composition is phthalate-free.

The present polymerization process and/or the present composition may comprise two or more embodiments disclosed herein.

The composition may be formed into an article. In an embodiment, an article is provided and includes a composition of propylene-based polymer and a substituted phenylene aromatic diester. The composition includes any of the foregoing propylene-based polymers.

In an embodiment, the article is a molded article. Nonlimiting examples of molded articles include an injected molded article, an extruded article, a thermoformed article, and a blow molded article. In an embodiment, the article may be composed of nucleated propylene-based polymer or non-nucleated propylene-based polymer. Nonlimiting examples of suitable articles include film (cast film and/or blown film), fiber (continuous filaments, spunbond filaments, melt flown filaments and stretched filaments), pipe, tubing, cable, sheet, cups, pails, bottles, containers, boxes, automotive parts, appliances, consumer goods, closures, and lids.

In an embodiment, the procatalyst composition, the polymer composition produced therefrom, and/or articles composed of the polymeric composition produced from the procatalyst composition is/are phthalate-free, or is/are otherwise void or devoid of phthalate and/or phthalate derivatives.

The present article may comprise two or more embodiments disclosed herein.

DEFINITIONS

All references to the Periodic Table of the Elements herein shall refer to the Periodic Table of the Elements, published and copyrighted by CRC Press, Inc., 2003. Also, any references to a Group or Groups shall be to the Groups or Groups reflected in this Periodic Table of the Elements using the IUPAC system for numbering groups. Unless stated to the contrary, implicit from the context, or customary in the art, all parts and percents are based on weight. For purposes of United States patent practice, the contents of any patent, patent application, or publication referenced herein are hereby incorporated by reference in their entirety (or the equivalent US version thereof is so incorporated by reference), especially with respect to the disclosure of synthetic techniques, definitions (to the extent not inconsistent with any definitions provided herein) and general knowledge in the art.

The term "comprising," and derivatives thereof, is not intended to exclude the presence of any additional component, step or procedure, whether or not the same is disclosed herein. In order to avoid any doubt, all compositions claimed herein through use of the term "comprising" may include any additional additive, adjuvant, or compound whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination.

Any numerical range recited herein, includes all values from the lower value to the upper value, in increments of one unit, provided that there is a separation of at least 2 units between any lower value and any higher value. As an example, if it is stated that the amount of a component, or a value of a compositional or a physical property, such as, for example, amount of a blend component, softening temperature, melt index, etc., is between 1 and 100, it is intended that all individual values, such as, 1, 2, 3, etc., and all subranges, such as, 1 to 20, 55 to 70, 197 to 100, etc., are expressly enumerated in this specification. For values which are less than one, one unit is considered to be 0.0001, 0.001, 0.01 or 0.1, as appropriate. These are only examples of what is specifically intended, and all possible combinations of numerical values between the lowest value and the highest value enumerated, are to be considered to be expressly stated in this application. In other words, any numerical range recited herein includes any value or subrange within the stated range. Numerical ranges have been recited, as discussed herein, reference melt index, melt flow rate, and other properties.

The terms "blend" or "polymer blend," as used herein, is a blend of two or more polymers. Such a blend may or may not be miscible (not phase separated at molecular level). Such a blend may or may not be phase separated. Such a blend may or may not contain one or more domain configurations, as determined from transmission electron spectroscopy, light scattering, x-ray scattering, and other methods known in the art.

The term "composition," as used herein, includes a mixture of materials which comprise the composition, as well as reaction products and decomposition products formed from the materials of the composition.

The term "polymer" is a macromolecular compound prepared by polymerizing monomers of the same or different type. "Polymer" includes homopolymers, copolymers, terpolymers, interpolymers, and so on. The term "interpolymer" means a polymer prepared by the polymerization of at least two types of monomers or comonomers. It includes, but is not limited to, copolymers (which usually refers to polymers prepared from two different types of monomers or comonomers, terpolymers (which usually refers to polymers prepared from three different types of monomers or comonomers), tetrapolymers (which usually refers to polymers prepared from four different types of monomers or comonomers), and the like.

The term "olefin-based polymer" is a polymer containing, in polymerized form, a majority weight percent of an olefin, for example ethylene or propylene, based on the total weight of the polymer. Nonlimiting examples of olefin-based polymers include ethylene-based polymers and propylene-based polymers.

The term, "propylene-based polymer," as used herein, refers to a polymer that comprises a majority weight percent polymerized propylene monomer (based on the total amount of polymerizable monomers), and optionally may comprise at least one polymerized comonomer.

The term "alkyl," as used herein, refers to a branched or unbranched, saturated or unsaturated acyclic hydrocarbon radical. Nonlimiting examples of suitable alkyl radicals include, for example, methyl, ethyl, n-propyl, i-propyl, 2-propenyl (or allyl), vinyl, n-butyl, t-butyl, i-butyl (or 2-methylpropyl), etc. The alkyls have 1 and 20 carbon atoms.

The term "substituted alkyl," as used herein, refers to an alkyl as just described in which one or more hydrogen atom bound to any carbon of the alkyl is replaced by another group such as a halogen, aryl, substituted aryl, cycloalkyl, substituted cycloalkyl, heterocycloalkyl, substituted heterocycloalkyl, halogen, haloalkyl, hydroxy, amino, phosphido, alkoxy, amino, thio, nitro, and combinations thereof. Suitable substituted alkyls include, for example, benzyl, trifluoromethyl and the like.

The term "aryl," as used herein, refers to an aromatic substituent which may be a single aromatic ring or multiple aromatic rings which are fused together, linked covalently, or linked to a common group such as a methylene or ethylene moiety. The aromatic ring(s) may include phenyl, naphthyl, anthracenyl, and biphenyl, among others. The aryls have 1 and 20 carbon atoms.

Test Methods $^{13}C$ NMR characterization (ethylene content, Koenig B-value, triad distribution, triad tacticity, number average sequence length for ethylene and propylene (i.e., le and lp respectively) is performed as follows:

Sample Preparation

The samples are prepared by adding approximately 2.7 g of a 50/50 mixture of tetrachloroethane-$d_2$/orthodichlorobenzene containing 0.025 M Cr(AcAc)$_3$ to 0.20 g sample in a Norell 1001-7 10 mm NMR tube. The samples are dissolved and homogenized by heating the tube and its contents to 150° C. using a heating block and heat gun. Each sample is visually inspected to ensure homogeneity.

Data Acquisition Parameters

The data are collected using a Bruker 400 MHz spectrometer equipped with a Bruker Dual DUL high-temperature CryoProbe. The data are acquired using 1280 transients per data file, a 6 sec pulse repetition delay, 90 degree flip angles, and inverse gated decoupling with a sample temperature of 120° C. All measurements are made on non-spinning samples in locked mode. Samples are allowed to thermally equilibrate for 7 minutes prior to data acquisition Flexural modulus is determined in accordance with ASTM D790-00 Method 1, using an ASTM D 638 specimen tested at 1.3 mm/min.

Gel Permeation Chromatography (GPC) Analytical Method for Polypropylene. The polymers are analyzed on a PL-220 series high temperature gel permeation chromatography (GPC) unit equipped with a refractometer detector and four PLgel MixeD A (20 μm) columns (Polymer Laboratory Inc.). The oven temperature is set at 150° C. and the temperatures of autosampler's hot and the warm zones are at 135° C. and 130° C. respectively. The solvent is nitrogen purged 1,2,4-trichlorobenzene (TCB) containing ~200 ppm 2,6-di-t-butyl-4-methylphenol (BHT). The flow rate is 1.0 mL/min and the injection volume was 200 μl. A 2 mg/mL sample concentration is prepared by dissolving the sample in $N_2$ purged and preheated TCB (containing 200 ppm BHT) for 2.5 hrs at 160° C. with gentle agitation.

The GPC column set is calibrated by running twenty narrow molecular weight distribution polystyrene standards. The molecular weight (MW) of the standards ranges from 580 to 8,400,000 g/mol, and the standards were contained in 6 "cocktail" mixtures. Each standard mixture has at least a decade of separation between individual molecular weights. The polystyrene standards are prepared at 0.005 g in 20 mL of solvent for molecular weights equal to or greater than 1,000,000 g/mol and 0.001 g in 20 mL of solvent for molecular weights less than 1,000,000 g/mol. The polystyrene standards are dissolved at 150° C. for 30 min under stirring. The narrow standards mixtures are run first and in order of decreasing highest molecular weight component to minimize degradation effect. A logarithmic molecular weight calibration is generated using a forth-order polynomial fit as a function of elution volume. The equivalent polypropylene molecular weights are calculated by using following equation with reported Mark-Houwink coefficients for polypropylene (Th.G. Scholte, N. L. J. Meijerink, H. M. Schoffeleers, and A. M. G. Brands, J. Appl. Polym. Sci., 29, 3763-3782 (1984)) and polystyrene (E. P. Otocka, R. J. Roe, N. Y. Hellman, P. M. Muglia, Macromolecules, 4, 507 (1971)):

$$M_{PP} = \left(\frac{K_{PS} M_{PS}^{a_{PS}+1}}{K_{PP}}\right)^{\frac{1}{a_{PP}+1}}$$

where $M_{PP}$ is PP equivalent MW, $M_{PS}$ is PS equivalent MW, log K and a values of Mark-Houwink coefficients for PP and PS are listed below in Table 1.

TABLE 1

| Polymer | A | log K |
|---|---|---|
| Polypropylene | 0.725 | −3.721 |
| Polystyrene | 0.702 | −3.900 |

Isotaticity is measured using a Bruker 400 MHz spectrometer equipped with a Bruker Dual DUL high-temperature CryoProbe. The data is acquired using 320 transients per data file, a 6 sec pulse repetition delay (4.7 s delay+1.3 s acq. time), 90 degree flip angles, and inverse gated decoupling with a sample temperature of 120° C. All measurements are made on non-spinning samples in locked mode. Samples are homogenized immediately prior to insertion into the heated (125° C.) NMR Sample changer, and are allowed to thermally equilibrate in the probe for 7 minutes prior to data acquisition. The $^{13}C$ NMR chemical shifts are internally referenced to the mmmm isotactic pentad at 21.90 ppm.

Izod impact strength is measured in accordance with ASTM D 256.

Liso (isotactic block length) is defined by the following equation:

(2*mmmm/mmrr)+3.

Melt flow rate (MFR) is measured in accordance with ASTM D 1238-01 test method at 230° with a 2.16 kg weight for propylene-based polymers.

Molecular weights (Mn, Mw and Mz) and MWD's (Mw/Mn and Mz/Mw) are measured by GPC. Polystyrene standards are used for calibration.

Oligomer content is measured by extracting 0.5 g of polymer with 5 g of chloroform for 12 hours at room temperature. The extract is injected into an Agilent 6890 Gas Chromatographer with a flame ionization detector (Agilent Technologies, Inc., Wilmington, Del.). The column is a 30 m×0.25 mm i.d. fused silica capillary; 0.25 µM film thickness of methyl silicon (DB-1). The oven is operated at an initial temperature of 50° C. for 4 minutes, program to 340° C. at 10° C./minute and held for 30 minutes. The oligomer quantification was done by comparing to an internal hexadecane standard.

Polydispersity Index (PDI) is measured using a Rheometrics 800 cone and plate rheometer from TA Instruments, operated at 180° C., using the method of Ziechner and Patel, (1981) "A Comprehensive Study of Polypropylene Melt Rheology" Proc. of the $2^{nd}$ World Congress of Chemical Eng., Montreal, Canada. In this method the cross-over modulus is determined, and the PDI defined as 100,000/cross-over modulus (in Pascals).

Xylene Solubles (XS) is measured according to the following procedure: 0.4 g of polymer is dissolved in 20 ml of xylenes with stirring at 130° C. for 30 minutes. The solution is then cooled to 25° C. and after 30 minutes the insoluble polymer fraction is filtered off. The resulting filtrate is analyzed by Flow Injection Polymer Analysis using a Viscotek ViscoGEL H-100-3078 column with THF mobile phase flowing at 1.0 ml/min. The column is coupled to a Viscotek Model 302 Triple Detector Array, with light scattering, viscometer and refractometer detectors operating at 45° C. Instrument calibration was maintained with Viscotek PolyCAL™ polystyrene standards.

By way of example and not by limitation, examples of the present disclosure will now be provided.

I. Catalysts

1. Substituted Phenylene Aromatic Diester.

Substituted phenylene aromatic diester may be synthesized in accordance with U.S. patent application Ser. No. 61/141,959 filed on Dec. 31, 2008, the entire content of which is incorporated by reference herein. Nonlimiting examples of suitable substituted phenylene aromatic diester are provided in Table 2 below.

TABLE 2

| Compound | Structure | $^1$H NMR (500 MHz, CDCl$_3$, ppm) |
|---|---|---|
| 3-methyl-5-tert-butyl-1,2-phenylene dibenzoate | 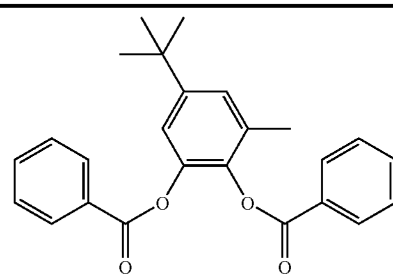 | δ 8.08 (dd, 2H), 8.03 (dd, 2H), 7.53 (tt, 1H), 7.50 (tt, 1H), 7.38 (t, 2H), 7.34 (t, 2H), 7.21 (d, 1H), 7.19 (d, 1H), 2.28 (s, 3H), 1.34 (s, 9H). |
| 3,5-diisopropyl-1,2-phenylene dibenzoate | 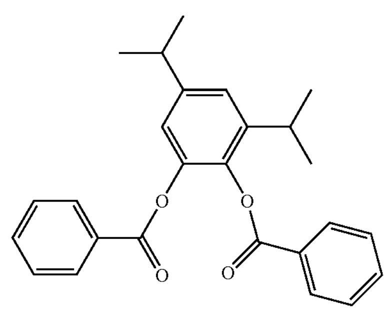 | δ 8.08 (dd, 2H), 7.00 (dd, 2H), 7.53 (tt, 1H), 7.48 (tt, 1H), 7.39 (t, 2H), 7.31 (t, 2H), 7.11 (d, 1H), 7.09 (d, 1H), 3.11 (heptat, 1H), 2.96 (heptat, 1H), 1.30 (d, 6H), 1.26 (d, 6H). |
| 3,6-dimethyl-1,2-phenylene dibenzoate | 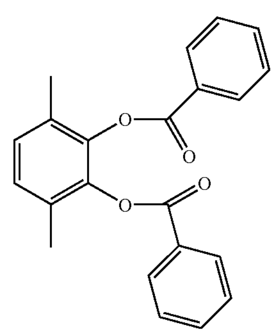 | δ 8.08 (d, 2H), 7.51 (t, 1H), 7.34 (d, 2H), 7.11 (s, 2H), 2.23 (s, 6H). |

TABLE 2-continued

| Compound | Structure | $^1$H NMR (500 MHz, CDCl$_3$, ppm) |
|---|---|---|
| 3-methyl-5-tert-butyl-1,2-phenylene dibenzoate | 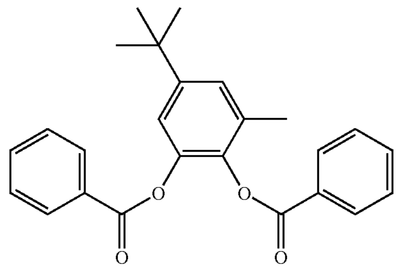 | δ 8.08 (dd, 2H), 8.03 (dd, 2H), 7.53 (tt, 1H), 7.50 (tt, 1H), 7.38 (t, 2H), 7.34 (t, 2H), 7.21 (d, 1H), 7.19 (d, 1H), 2.28 (s, 3H), 1.34 (s, 9H). |
| 3,5-diisopropyl-1,2-phenylene dibenzoate | 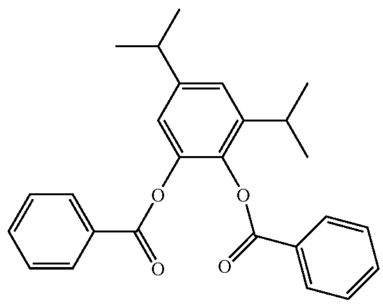 | δ 8.08 (dd, 2H), 7.00 (dd, 2H), 7.53 (tt, 1H), 7.48 (tt, 1H), 7.39 (t, 2H), 7.31 (t, 2H), 7.11 (d, 1H), 7.09 (d, 1H), 3.11 (heptat, 1H), 2.96 (heptat, 1H), 1.30 (d, 6H), 1.26 (d, 6H). |
| 4-t-butyl-1,2-phenylene dibenzoate | 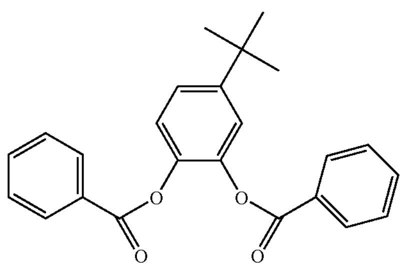 | δ 8.07 (dd, 4H), 7.54 (m, 2H), 7.30-7.40 (m, 7H), 1.37 (s, 9H). |
| 4-methyl 1,2-phenylene dibenzoate | 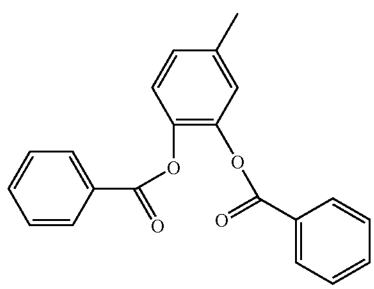 | δ (ppm) 8.07 (d, 4H), 7.54 (t, 2H), 7.37 (t, 4H), 7.27 (d, 1H), 7.21 (s, 1H), 7.15 (d, 1H), 2.42 (s, 3H). |
| 1,2-naphthalene dibenzoate | 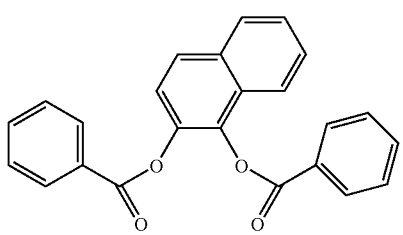 | δ 8.21-8.24 (m, 2H), 8.08-8.12 (m, 2H), 7.90-7.96 (m, 2H), 7.86 (d, 1H), 7.60 (m, 1H), 7.50-7.55 (m, 4H), 7.46 (t, 2H), 7.37 (t, 2H). |

TABLE 2-continued

| Compound | Structure | $^1$H NMR (500 MHz, CDCl$_3$, ppm) |
| --- | --- | --- |
| 3-methyl-5-tert-butyl-1,2-phenylene dibenzoate | 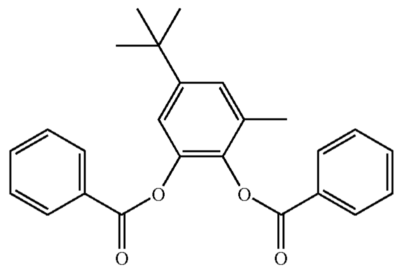 | δ 8.08 (dd, 2H), 8.03 (dd, 2H), 7.53 (tt, 1H), 7.50 (tt, 1H), 7.38 (t, 2H), 7.34 (t, 2H), 7.21 (d, 1H), 7.19 (d, 1H), 2.28 (s, 3H), 1.34 (s, 9H). |
| 3,5-diisopropyl-1,2-phenylene dibenzoate | 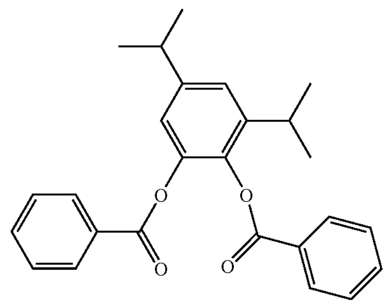 | δ 8.08 (dd, 2H), 7.00 (dd, 2H), 7.53 (tt, 1H), 7.48 (tt, 1H), 7.39 (t, 2H), 7.31 (t, 2H), 7.11 (d, 1H), 7.09 (d, 1H), 3.11 (heptat, 1H), 2.96 (heptat, 1H), 1.30 (d, 6H), 1.26 (d, 6H). |
| 2,3-naphthalene dibenzoate | 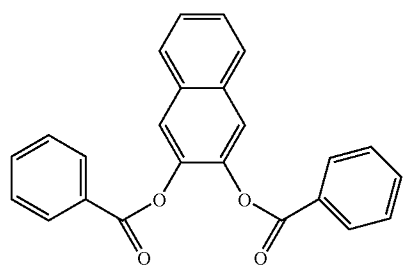 | δ 8.08-8.12 (m, 4H), 7.86-7.90 (m, 4H), 7.51-7.58 (m, 4H), 7.38 (t, 4H) |
| 3-methyl-5-tert-butyl-1,2-phenylene di(4-methylbenzoate) | 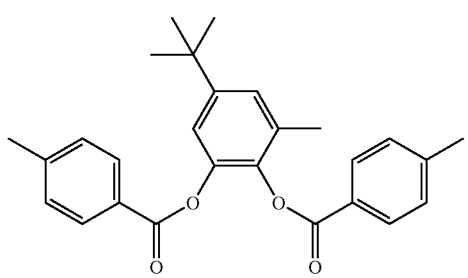 | δ (ppm) 7.98 (d, 2H), 7.93 (d, 2H), 7.18 (d, 4H), 7.15 (d, 2H), 2.38 (s, 3H), 2.36 (s, 3H), 2.26 (s, 3H), 1.35 (s, 9H). |
| 3-methyl-5-tert-butyl-1,2-phenylene di(2,4,6-trimethylbenzoate) | 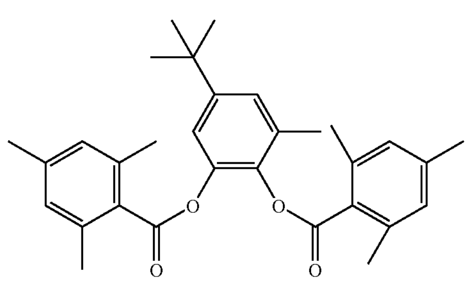 | δ (ppm) 7.25 (s, 1H), 7.21 (s, 1H), 6.81 (d, 4H), 2.36 (s, 3H), 2.30 (d, 6H), 2.25 (s, 6H), 2.23 (s, 6H), 1.36 (s, 9H). |

TABLE 2-continued

| Compound | Structure | $^1$H NMR (500 MHz, CDCl$_3$, ppm) |
|---|---|---|
| 3-methyl-5-tert-butyl-1,2-phenylene di(4-fluorobenzoate) | *(structure)* | δ 7.98 (dd, 4H), 7.36 (dd, 4H), 7.21 (s, 1H), 7.17 (s, 1H), 2.26 (s, 3H), 1.34 (s, 9H). |
| 3-methyl-5-tert-butyl-1,2-phenylene dibenzoate | *(structure)* | δ 8.08 (dd, 2H), 8.03 (dd, 2H), 7.53 (tt, 1H), 7.50 (tt, 1H), 7.38 (t, 2H), 7.34 (t, 2H), 7.21 (d, 1H), 7.19 (d, 1H), 2.28 (s, 3H), 1.34 (s, 9H). |
| 3,5-diisopropyl-1,2-phenylene dibenzoate | *(structure)* | δ 8.08 (dd, 2H), 7.00 (dd, 2H), 7.53 (tt, 1H), 7.48 (tt, 1H), 7.39 (t, 2H), 7.31 (t, 2H), 7.11 (d, 1H), 7.09 (d, 1H), 3.11 (heptat, 1H), 2.96 (heptat, 1H), 1.30 (d, 6H), 1.26 (d, 6H). |
| 3-methyl-5-tert-butyl-1,2-phenylene di(4-chlorobenzoate) | *(structure)* | δ 7.98 (dd, 4H), 7.36 (dd, 4H), 7.21 (s, 1H), 7.17 (s, 1H), 2.26 (s, 3H), 1.34 (s, 9H). |

2. SHAC 320

II. Procatalyst Compositions

At ambient temperature, 351 g of a mixed magnesium/titanium halide alcoholate is agitated in a mixture of 1.69 kg of chlorobenzene and 4.88 kg of titanium(IV) chloride. After 10 minutes, 750 mL of a chlorobenzene solution containing 164.5 g of 5-tert-butyl-3-methyl-1,2-phenylene dibenzoate is added, followed by an additional 0.46 kg of chlorobenzene. The mixture is agitated at 100° C. for 60 minutes, allowed to settle, then filtered at 100° C. The solids are agitated in 3.16 kg of chlorobenzene at 70° C. for 15 minutes, allowed to settle, then filtered at 70° C. The solids are agitated in a mixture of 2.36 kg of chlorobenzene and 4.84 kg of titanium (IV) chloride, and after 10 minutes, a solution of 109.7 g of 5-tert-butyl-3-methyl-1,2-phenylene dibenzoate in 416 g of chlorobenzene is added, followed by an additional 0.20 kg of chlorobenzene. The mixture is agitated at 105-110° C. for 30 minutes, allowed to settle, then filtered at 105-110° C. The solids are agitated in a mixture of 3.10 kg of chlorobenzene and 4.84 kg of titanium(IV) chloride at 105-110° C. for 30 minutes, allowed to settle, then filtered at 105-110° C. After cooling, the solids are washed twice with 3.47 kg of hexane at 45° C., followed by a final wash with 3.47 kg of 2-methylbutane at ambient temperature. The solids are subjected to vacuum to remove residual volatiles, then combined with 683 g of mineral to generate a slurry.

III. Polymerization

Polymerization is performed in a gas phase fluidized bed polymerization reactor (14-inch reactor diameter). The cocatalyst is triethylaluminum, the external electron donor is dicyclopentyldimethoxysilane (DCPDMS), or n-propyltriethoxysilane (PTES), and the activity limiting agent is isopropyl myristate (IPM). Specific reactor conditions an resultant polymer properties are provided in Table 3 below.

Example C is provided as a comparison and is not an embodiment of the present disclosure. Example C is a propylene homopolymer produced from a SHAC 320 procatalyst composition. SHAC 320 is a Ziegler-Natta procatalyst composition composed of titanium and magnesium and an internal electron donor of di-isobutylphthalate and prepared according to example 1 in U.S. Pat. No. 6,825,146, the entire content of which is incorporated by reference herein.

Typically, higher stiffness is achieved by increasing the PDI. The present propylene-based polymer produced surprisingly and unexpectedly exhibits high stiffness with a PDI less than 5.0. Example A has a PDI of 4.95, a xylene soluble content of 1.1 wt. % and a flexural modulus of about 283 kpsi. Surprisingly, high stiffness is achieved even though the PDI is less than 5.0, and as low as 4.0. Nucleation can be used to further increase the stiffness of the present propylene-based polymer.

TABLE 3

|  | A | B | C | D | E |
| --- | --- | --- | --- | --- | --- |
| Melt Flow (dg/min) | 50 | 45 | 58 | 216 | 367 |
| Xylene solubles (wt. %) | 1.1 | 1.5 | 1.5 | 1.5 | 1.9 |
| Catalyst | 1 | 1 | SHAC 320 | 1 | 1 |
| Rx 1 $H_2/C_3$ | 0.114 | 0.089 | 0.133 | 0.161 | 0.161 |
| Rx Temp (C) | 70 | 70 | 70 | 70 | 70 |
| Molar Al/DCPDMS | 3.98 | 5.75 | 5.70 | 5.50 | 20.00 |
| Molar/Al/PTES | — | — | — | — | 8.57 |
| Molar/Al/IPM | 2.65 | 3.83 | 3.80 | 3.68 | 4.00 |
| Rx 1 Al/Ti molar | 44 | 44 | 46 | 44 | 42 |
| Propylene partial pressure (kPa) | 320 | 320 | 320 | 320 | 320 |
| Rx 1 residence time (hours) | 2.7 | 2.8 | 2.7 | 2.5 | 2.1 |
| 1% SFM (kpsi) | 283.1 | 250.7 | 256.2 |  |  |
| RT Izod (ft-lb/in) | 0.36 | 0.35 | 0.38 |  |  |
| A-C nucleated with 1000 ppmw NA-11 |  |  |  |  |  |
| 1% SFM (kpsi) | 344.6 | 331.2 | 320.5 |  |  |
| RT Izod (ft-lb/in) | 0.4 | 0.39 | 0.38 |  |  |
| PDI (Cone & Plate) | 4.95 | 5.03 | 4.92 |  |  |
| Mn | 28,310 | 22,500 | 24,320 | 21,210 | 17,170 |
| Mw | 192,400 | 195,500 | 181,600 | 130,800 | 122,800 |
| Mz | 755,800 | 844,500 | 630,300 | 487,500 | 611,600 |
| Mw/Mn | 6.80 | 8.69 | 7.47 | 6.17 | 7.15 |
| Mz/Mw | 3.93 | 4.32 | 3.47 | 3.73 | 4.98 |
| Oligomer |  |  |  |  |  |
| C12 (ppmw) | 243 | 277 | 428 |  |  |
| C15 (ppmw) | 279 | 335 | 547 |  |  |
| C18 (ppmw) | 285 | 350 | 531 |  |  |
| C21 (ppmw) | 302 | 350 | 523 |  |  |
| Sum (C12-21, ppmw) | 1109 | 1312 | 2029 |  |  |
| NMR |  |  |  |  |  |
| mmmm % | 97.4 | 96.6 | 96.2 |  |  |
| mm % | 98.8 | 98.3 | 98 |  |  |
| Liso | 530 | 310 | 335 |  |  |

DCPDMS = dicyclopentyldimethoxysilane
PTES = n-propyltriethoxysilane
IPM = isopropyl myristate Examples A-C are compounded with the additives listed in Table 4 using 25 mm W&P twin screw extruders.

TABLE 4

| Additives (ppmw) | Samples A-C |
| --- | --- |
| Irganox 1010 (hindered phenolic antioxidant) | 1000 |
| Irgafos 168 (Phosphite Antioxidant) | 1000 |
| Calcium Stearate (acid acceptor) | 600 |
| NA-11 - nucleating agent | 1000 |

Surprisingly and unexpectedly, Example A, which is produced using a molar Al/DCPDMS ratio of less than 5.0 in conjunction with substituted phenylene aromatic diester internal electron donor, has a higher flexural modulus and a lower xylene soluble content than comparative Example C.

It is specifically intended that the present disclosure not be limited to the embodiments and illustrations contained herein, but include modified forms of those embodiments including portions of the embodiments and combinations of elements of different embodiments as come within the scope of the following claims.

What is claimed is:

1. A composition comprising:
   a propylene homopolymer; and
   a substituted phenylene aromatic diester that is 3-methyl-5-tert butyl-1,2 phenylene dibenzoate.

2. The composition of claim 1 wherein the propylene homopolymer has a flexural modulus of greater than 260 kpsi as determined by ASTM D 790.

3. The composition of claim 1 wherein the propylene homopolymer is nucleated.

4. The composition of claim 3 wherein the nucleated propylene homopolymer has a flexural modulus of greater than 322 kpsi as determined by ASTM D 790.

5. The composition of claim 1 wherein the propylene homopolymer has a polydispersity index of 8.0 or less.

6. The composition of claim 1 wherein the propylene homopolymer has a xylene soluble content less than or equal to 1.5% by weight.

7. The composition of claim 1 wherein the propylene homopolymer has isotactic (mmmm) pentads higher than 97%, as determined by $^{13}$C-NMR analysis.

8. The composition of claim 1 wherein the propylene homopolymer has a melt flow rate from 50 g/10 min to 100 g/10 min as measured in accordance with ASTM D 1238 (230° C., 2.16 kg).

9. The composition of claim 1 wherein the propylene homopolymer has a melt flow rate of 50 g/10 min and an oligomer content less than 1800 ppmw.

10. A composition comprising:
a non-nucleated propylene homopolymer comprising a substituted phenylene aromatic diester comprising 3-methyl-5-tert butyl-1,2 phenylene dibenzoate and having a polydispersity index less than 6.0, a flexural modulus greater than 283 kpsi and a melt flow rate greater than or equal to 50 g/10 min as measured in accordance with ASTM D 1238 (230° C., 2.16 kg); and an oligomer content of less than 1800 ppmw.

11. The composition of claim 10 wherein the propylene-based polymer has a xylene soluble content less than or equal to 1.5% by weight.

12. A propylene impact copolymer comprising:
a propylene homopolymer;
a propylene/ethylene copolymer dispersed within the propylene homopolymer; and
a substituted phenylene aromatic diester that is 3-methyl-5-tert butyl-1,2 phenylene dibenzoate.

13. The propylene impact copolymer of claim 12 wherein the substituted phenylene aromatic diester is present in the propylene homopolymer.

14. The propylene impact copolymer of claim 12 wherein the substituted phenylene aromatic diester is present in the propylene/ethylene copolymer.

* * * * *